United States Patent
Woolf et al.

(10) Patent No.: US 11,432,528 B2
(45) Date of Patent: *Sep. 6, 2022

(54) DEVICES AND METHODS FOR ANALYZING RODENT BEHAVIOR

(71) Applicants: Children's Medical Center Corporation, Boston, MA (US); President and Fellows of Harvard College, Cambridge, MA (US)

(72) Inventors: Clifford J. Woolf, Newton, MA (US); David P. Roberson, Cambridge, MA (US); Alexander B. Wiltschko, Boston, MA (US); Sandeep Robert Datta, Newton, MA (US)

(73) Assignees: President and Fellows of Harvard College, Cambridge, MA (US); Children's Medical Center Corporation, Boston, MA (US)

( * ) Notice: Subject to any disclaimer, the term of this patent is extended or adjusted under 35 U.S.C. 154(b) by 542 days.

This patent is subject to a terminal disclaimer.

(21) Appl. No.: 16/275,810

(22) Filed: Feb. 14, 2019

(65) Prior Publication Data

US 2019/0261596 A1    Aug. 29, 2019

Related U.S. Application Data

(63) Continuation of application No. 15/032,730, filed as application No. PCT/US2014/063400 on Oct. 31, 2014, now Pat. No. 10,238,085.
(Continued)

(51) Int. Cl.
*A01K 29/00* (2006.01)
*A61B 5/11* (2006.01)
(Continued)

(52) U.S. Cl.
CPC ............ *A01K 1/031* (2013.01); *A01K 29/005* (2013.01); *A61B 5/1038* (2013.01);
(Continued)

(58) Field of Classification Search
CPC .... A01K 29/005; A01K 1/031; A61B 5/1038; A61B 5/1128; A61B 5/1105
See application file for complete search history.

(56) References Cited

U.S. PATENT DOCUMENTS 3,304,911 A * 2/1967 Hakata ................ A61B 5/1105
119/421
3,974,798 A    8/1976 Meetze, Jr.
(Continued)

FOREIGN PATENT DOCUMENTS

CN      201019748 Y    2/2008
WO   WO 03/025615 A2   3/2003
(Continued)

OTHER PUBLICATIONS

Chen et al., Detection of subtle neurological alterations by the Catwalk XT gait analysis system. Journal of neuroengineering and rehabilitation. Dec. 2014;11(1):62.
(Continued)

*Primary Examiner* — Magdalena Topolski
(74) *Attorney, Agent, or Firm* — Wolf, Greenfield & Sacks, P.C.

(57) ABSTRACT

A device for detecting and recording animal behavior may include at least one corral that defines a contained field, the base surface of the at least one corral being sensitive to the animal's footprint. The device also includes an image capturing device that cooperates with the base surface to capture both a profile of the animal's full footprint and a profile of the animal's toe print when the animal is standing on its toes. In some embodiments, the device is capable of providing a
(Continued)

stimulus to the animal and observing the resulting behavior of the animal via the image capturing device.

21 Claims, 19 Drawing Sheets

Related U.S. Application Data

(60) Provisional application No. 61/898,754, filed on Nov. 1, 2013.

(51) Int. Cl.
*A01K 1/03* (2006.01)
*A61B 5/103* (2006.01)
*G06T 7/20* (2017.01)

(52) U.S. Cl.
CPC .......... *A61B 5/1105* (2013.01); *A61B 5/1128* (2013.01); *G06T 7/20* (2013.01)

(56) References Cited

U.S. PATENT DOCUMENTS

| | | | |
|---|---|---|---|
| 4,574,734 | A | 3/1986 | Mandalaywala et al. |
| 4,858,621 | A | 8/1989 | Franks |
| 4,968,974 | A | 11/1990 | Sakano |
| 6,678,413 | B1 | 1/2004 | Liang et al. |
| 7,068,842 | B2 | 6/2006 | Liang et al. |
| 8,485,133 | B1* | 7/2013 | Osmekhin ............ A01K 1/031 119/421 |
| 8,514,236 | B2 | 8/2013 | Kobla et al. |
| 8,634,635 | B2 | 1/2014 | Bai et al. |
| 10,238,085 | B2 | 3/2019 | Woolf et al. |
| 2003/0004652 | A1 | 1/2003 | Brunner et al. |
| 2003/0055362 | A1 | 3/2003 | Hampton |
| 2003/0206287 | A1 | 11/2003 | McClurg et al. |
| 2005/0163349 | A1 | 7/2005 | Brunner et al. |
| 2006/0107066 | A1 | 5/2006 | Cova et al. |
| 2007/0021421 | A1 | 1/2007 | Hampton |
| 2010/0111359 | A1 | 5/2010 | Bai et al. |
| 2010/0143265 | A1 | 6/2010 | Hewes et al. |
| 2010/0175629 | A1 | 7/2010 | Garmon |
| 2010/0217157 | A1 | 8/2010 | Tasch |
| 2010/0246902 | A1 | 9/2010 | Rowe et al. |
| 2010/0317094 | A1 | 12/2010 | Ricco et al. |
| 2012/0180731 | A1 | 7/2012 | Garner et al. |
| 2012/0293631 | A1 | 11/2012 | Schwarz et al. |
| 2014/0251228 | A1 | 9/2014 | Jensen-Jarolim et al. |
| 2016/0150758 | A1 | 6/2016 | Salem et al. |
| 2016/0270364 | A1 | 9/2016 | Woolf et al. |
| 2016/0300123 | A1 | 10/2016 | Jewell et al. |
| 2017/0064929 | A1 | 3/2017 | Yakovenko |
| 2017/0111128 | A1 | 4/2017 | Hammerschmidt |
| 2017/0351898 | A1 | 12/2017 | Zhang |
| 2019/0080158 | A1 | 3/2019 | Roberson et al. |
| 2020/0060225 | A1 | 2/2020 | Roberson et al. |
| 2020/0060616 | A1* | 2/2020 | Malkut ............... A61B 5/6829 |

FOREIGN PATENT DOCUMENTS

| | | |
|---|---|---|
| WO | WO 2005/001768 A1 | 1/2005 |
| WO | WO 2007/071572 A1 | 6/2007 |

OTHER PUBLICATIONS

U.S. Appl. No. 16/608,086, filed Oct. 24, 2019, Roberson et al.
International Search Report and Written Opinion for International Application No. PCT/US2014/063400, dated Feb. 19, 2015.
International Preliminary Report on Patentability for International Application No. PCT/US2014/063400, dated May 12, 2016.
Extended European Search Report for European Application No. 14857344.7, dated Jun. 9, 2017.
[No Author Listed] Automatic Footprint Classification. Noldus. Last Accessed on Oct. 24, 2013 at http://www.noldus.com/CatWalk-XT/automatic-footprint-classification 1 page.
[No Author Listed] Behavioral Research Blog—CatWalk gait analysis versus treadmills. Noldus. http://info.noldus.com/bid/93553/CatWalk-gait-analysis-versus-treadmills; Retrieved from the WayBack Machine on Aug. 29, 2016, noting date of May 13, 2013. 2 pages.
[No Author Listed] CatWalk 7.1 versus CatWalk XT. Noldus. http://www.noldus.com/catwalk-71-versus-catwalk-xt-81; Retrieved from the WayBack Machine on Aug. 29, 2016, noting date of Oct. 24, 2013. 2 pages.
[No Author Listed] CatWalktmXT. Noldus. Last Accessed on Oct. 24, 2013 at http://www.noldus.com/animal-behavior-research/products/catwalk 2 pages.
[No Author Listed] Discover CatWalk XT. Noldus. http://www.noldus.com/CatWalk-XT/specifications#; Retrieved from the WayBack Machine on Aug. 29, 2016, noting date of Oct. 24, 2013. 3 pages.
[No Author Listed] Illuminated Footprints Technology. http://www.noldus.com/CatWalk-XT/illuminated-footprints-technology; Retrieved from the WayBack Machine on Aug. 29, 2016, noting archive date of Oct. 24, 2013. 1 page.
[No Author Listed] New! CatWalk XT 10.5. Noldus. http://www.noldus.com/CatWalk-XT/new-features; Retrieved from the WayBack Machine of Aug. 29, 2016, noting date of Oct. 24, 2013. 4 pages.
[No Author Listed] Noldus—List of publications. Last Accessed on Oct. 24, 2013 at http://www.noldus.com/content/list-publications 3 pages.
Angeby-Möller et al., Using the CatWalk methof to assess weight-bearing and pain behaviour in walking rats with ankle joint monoarthritis induced by carrageenan: effects of morphine and rofecoxib. J Neurosci Methods. Sep. 15, 2008;174(1):1-9. doi: 10.1016/j.jneumeth.2008.06.017.
Betts et al., A device for measuring plantar pressures under the sole of the foot. IMechE. 1978;7(4):223-8.
Koopmans, CatWalk: the next step in gait analysis. Noldus. http://www.nolus.com/documentation/80; Retrieved from the WayBack Machine on Aug. 29, 2016, noting date of Oct. 24, 2013. 1 page.
Roedel et al., Effect of light or dark phase testing on behavioural and cognitive performance in DBA mice. Lab Anim. 2005;40:371-81.
Vrinten et al., 'CatWalk' automated quantitative gait analysis as a novel method to assess mechanical allodynia in the rat; a comparison with von Frey testing. Pain. Mar. 2003;102(1-2):203-9.

\* cited by examiner

DEVICES AND METHODS FOR ANALYZING RODENT BEHAVIOR

CROSS-REFERENCE TO RELATED APPLICATIONS

This application is a continuation of and claims priority under 35 U.S.C § 120 to U.S. application Ser. No. 15/032,730, filed Apr. 28, 2016, which is a national stage filing under 35 U.S.C. § 371 of International Application No. PCT/US2014/063400, entitled "DEVICES AND METHODS FOR ANALYZING RODENT BEHAVIOR and filed Oct. 31, 2014. International Application No. PCT/US2014/063400 claims the benefit under 35 U.S.C § 119(e) of U.S. Provisional Application Ser. No. 61/898,754, entitled "DEVICES AND METHODS FOR ANALYZING RODENT BEHAVIOR," filed Nov. 1, 2013. The entirety of each of the documents listed above is herein incorporated by reference.

FEDERALLY SPONSORED RESEARCH

This invention was made with U.S. Government support under Grant Nos. DP2 OD007109, RO1 DC011558, and PO1NS072040, each awarded by the National Institute of Health. The Government has certain rights in this invention.

FIELD

Devices and methods for analyzing rodent behavior are disclosed.

BACKGROUND

Rodent behavior detection and analysis may be a useful experimental tool, for example, to determine whether a certain medication, stimulus or environment has a consequence on the animal's behavior. Such information can be useful in developing treatments for use in other animals, including humans.

SUMMARY

Devices and methods for acquisition and analysis of animal behaviors are disclosed. Aspects disclosed herein relate to devices and methods that image the inferior surfaces (e.g., the plantar surface of paws, and inferior body parts) of freely behaving laboratory rodents in lit or dark conditions. This enables the identification and analysis of locomotion, gait, touch and pressure contact, nerve injury and regeneration, pain-like behavior, scratching, anxiety, aggression, social interaction, etc., of freely behaving rodents including mice and rats, either individually or in groups, and either in lit or dark environments. Conditions are observed via changes in the spatial extent, intensity and timing of the contact area of animal footpads and its relation to the rest of the body of the animal.

According to one aspect, a device for detecting and recording animal behavior is disclosed. The device includes at least one corral defining a contained field. A base surface of the at least one corral is sensitive to a footprint of the animal. An image capturing device cooperates with the base surface to capture both a profile of a full footprint of the animal (e.g., extent and intensity) and a profile of a toe print of a freely-behaving animal when the animal is standing on its toes, heels or footpads as well as by lighting the background or foreground to separately identify the position of the whole animal.

According to another aspect, a device for detecting and recording animal behavior is disclosed. The device includes a transparent base surface being sensitive to a footprint of the animal and an image capturing device beneath the base surface to capture both an image of a full footprint of the animal and an image of a toe print of the animal when the animal is standing on its toes. The device is adapted to provide a stimulus to the animal (e.g., by targeting light at the point of contact with the surface).

According to yet another aspect, a method of collecting behavioral information of a group of animals is disclosed. At least a subset of the group of animals is in a corral and is isolated from another subset of the group of animals. The method includes stimulating a first animal with a stimulus and observing a resulting behavior of the first animal via imaging both a footprint and a toe print of the first animal in response to the stimulus (e.g., imaging the spatial extent, pressure-related footprint intensity or timing of both the footprint and the toe print of the first animal). In some embodiments, the stimulus may include placing at least a subset of rodents in the same corral and observing the social interactions amongst the subset of rodents.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
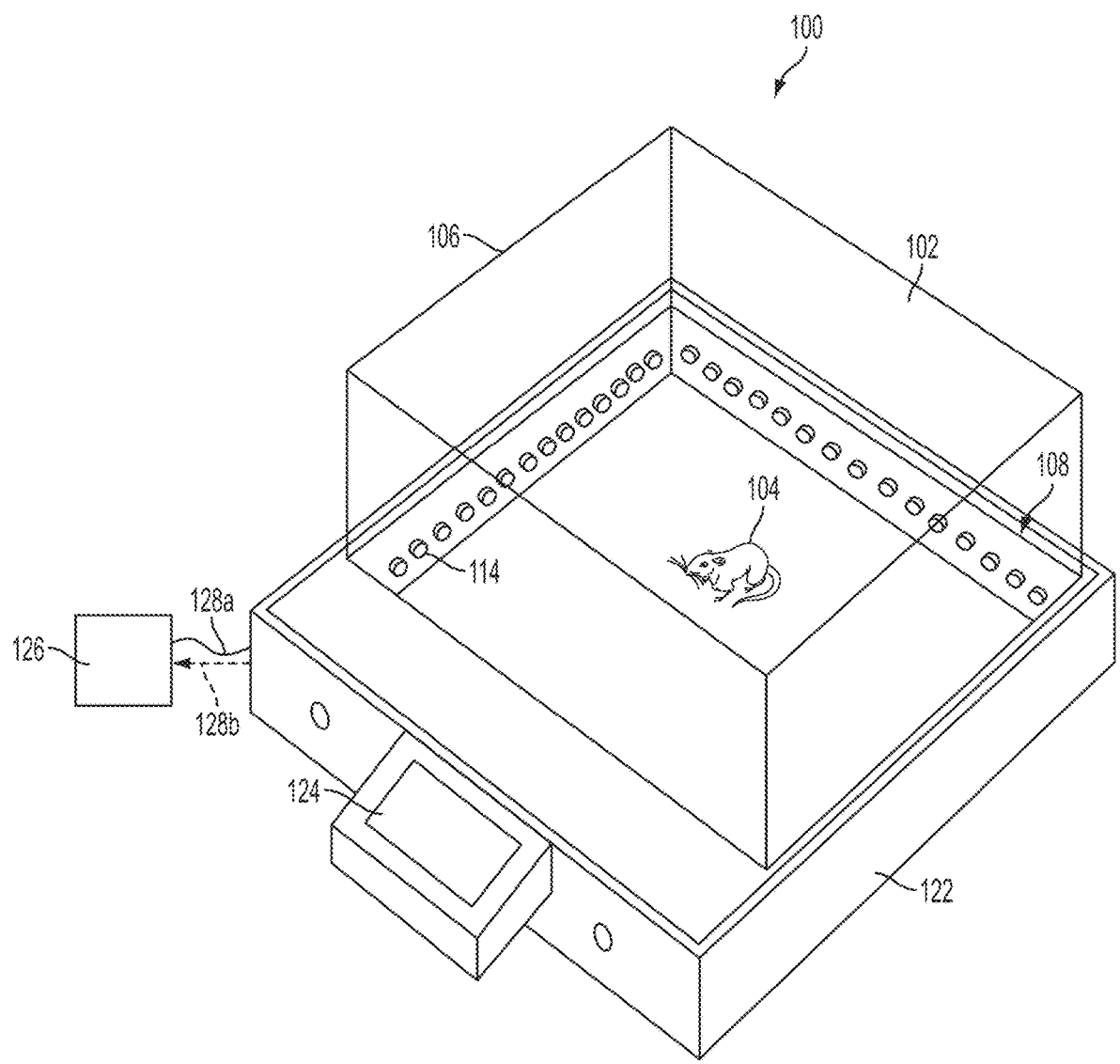
FIG. 1 is a perspective view of a device for monitoring animal behavior according to one embodiment.

Valuable information can be learned for laboratory studies by monitoring and analyzing the activity and motor performance of animals, e.g. rodents. One such application is the identification and analysis of locomotion, gait, touch and pressure against surfaces, nerve injury and regeneration, pain-like behavior, itch-like behavior, anxiety, aggression, and/or social interaction of the rodents. For example, identifying characteristic changes in gait that may accompany reactions to certain stimuli. Applicants have recognized that by monitoring the activity of freely behaving rodents, either individually or in groups, advantages may be realized. In some embodiments, the behavior of rodents is monitored after the rodents have been genetically modified and/or after the rodents are subjected to different types of stimulus in lit or dark environments.

According to one aspect, the voluntary and evoked movement of freely behaving animals, such as rodents, e.g., mice or rats, is monitored via a device capable of producing images of topographic features representing an inferior surface of the freely behaving animal. In some embodiments, this includes the spatial extent, intensity and dynamic changes of the surface. The inferior surface of the rodents may include a paw print, a toe print, or any other suitable inferior surface of the animal, e.g., a rodents' abdomen or tail. Without wishing to be bound by theory, freely behaving animals may include animals that are allowed to travel without obstruction within an area, such as a corral. It should be noted that such corral is not limited to an outdoor area for large animals; rather, as contemplated herein, a corral can be a test chamber for use with small animals, such as rodents (e.g., mice or rats).

In some embodiments, the device utilizes a horizontal contact sensor positioned above a capturing device, such as a video camera. In some embodiments, the contact sensor is a horizontal, transparent sensor. During experimentation, the subject animal may be contained within an open-bottom chamber and placed directly on top of the sensor, thus permitting the animal to roam freely on top of the sensor while being video recorded from below.

The sensor may be constructed based on the phenomenon of frustrated total internal reflection (FTIR) of band light. In some embodiments, the sensor is constructed based on FTIR of a non-visible band light, such as near-infrared, infrared, or ultraviolet light, although other suitable band light may be employed as this aspect of the disclosure is not limited in this regard. In one embodiment, the contact sensor includes a horizontally-positioned transparent glass or acrylic panel with a light source in the non-visible range. For example, infrared LED lights may be positioned around the perimeter of the panel (e.g., as strip lights or as lights mounted in a channel of a removable rail). Without wishing to be bound by theory, when the light strikes the medium boundary between the glass panel and the ambient air above the panel at an angle larger than the critical angle, the light is totally internally reflected and no light is emitted towards the camera below. Again, without wishing to be bound by theory, when an object, such as a mouse paw pad, having a higher refractive index than air comes within several wavelengths distance of the glass/air boundary, the evanescent wave passes light energy into the object, making it visible to the camera below. Stated another way, when the object, e.g. the mouse paw, comes into contact with the panel, the internally reflected light is "frustrated" and refracted out of the glass panel where it can be detected by a camera positioned below the glass panel. In some embodiments, the intensity, contact area, spatial extent and position of the "frustrated" light signal and its change over time facilitates determining the physical and physiological aspects of the animal's behavior, such as the relative weight borne on each paw or the distribution of weight within each footprint. This, in turn, may provide an objective readout relating to the subjective experience of the animal.

In some embodiments, the non-visible band light facilitates monitoring of nocturnal behavior during the nighttime period when rodents are most active. Without wishing to be bound by theory, as the light is not visible to the animals, the animals are undisturbed, unless subjected to a stimulus, and thus are left to roam freely.

To facilitate observation of nocturnal behavior, the open-bottomed chamber may be made of an opaque material and the chamber area illuminated from a light source positioned under the panel or sensor using red, near-infrared or other lighting that is not visible to rodents. Similarly, a visible light source positioned beneath the sensor or panel may be used to illuminate the inferior surfaces of the animal that are not in contact with the sensor.

In other embodiments, the device is configured to deliver different types of stimulus to the freely roaming rodents and to examine the rodents' behavioral responses after application of the stimulus. In some embodiments, the stimulus includes thermal, mechanical, electric, audio, olfactory or smell, textural, or light stimulation, although other types of stimulation may be employed. In some embodiments, the stimulus is delivered via the sensor, although the stimulus may be delivered via other methods as this aspect of the disclosure is not limiting. A skilled artisan should appreciate that more than one stimulus (whether simultaneous or sequential) may be applied to a single animal during the course of an experiment. A person having skill in the art should further appreciate that different stimuli may be applied to each of the animals in a study when multiple animals are being tested.

In some embodiments, light stimulus may be delivered through the surface of the panel or sensor. For purposes herein, light stimulus may include the application of light to stimulate a genetically engineered, light sensitive animal and the application of light as a visual stimulus for any animal. For example, light stimulus may be applied by directing specific wavelengths of laser generated light at points on the animal body (e.g., the footpads) using a scanning mirror galvanometer or other laser pointing devices, or via LED arrays positioned below the sensor and generating specific light wavelengths directed through the sensor to the entire inferior surface of the animal body. Light stimulus also may be applied via LED arrays generating specific wavelengths of light that can be positioned to generate FTIR of light that is then delivered to the surfaces of the rodent body in contact or nearby the sensor. Without wishing to be bound by theory, delivery of light using these methods may permit control of specific peripheral nerve activity or cell function using light as stimulus while simultaneously imaging the mouse to acquire and analyze behavior data related to the light-activated nerve or cell activity. For example, light stimulus can be used for the manipulation of genetically encoded light-sensitive proteins to study function of molecules, synapses, cells and system or other light sensitive molecules engineered to interact or bind to cellular proteins. Also as an example, the expression of naturally occurring light-gated proteins (e.g., channelrhodopsins) or the introduction of light sensitive molecules in defined subsets of cells or proteins can address important questions about cells and systems into which they are introduced since they allow cellular activity, such as the activation of specific cell types or the opening of specific ion channels, to be performed in a targeted manner by the administration of light. Also, a chemical that binds to proteins and makes them light sensitive may be used. The applied light may be applied in different temporal patterns, different sizes and intensities for different durations in order to activate or inhibit specific neurons, proteins or receptors.

In some embodiments, the surface temperature of the sensor may be manipulated to explore behavioral responses to a thermal stimulus. In some embodiments, the glass or panel may have a thermally conductive layer or a thermally conductive plate may be used. The temperature also may be varied via an infrared heat source or via an infrared light source. In some embodiments, the temperature may be manually adjusted whereas in other embodiments it may be automatically adjustable. In some embodiments, the surface upon which the animal is freely roaming may have one or more textures to stimulate the animal.

Figure 2:
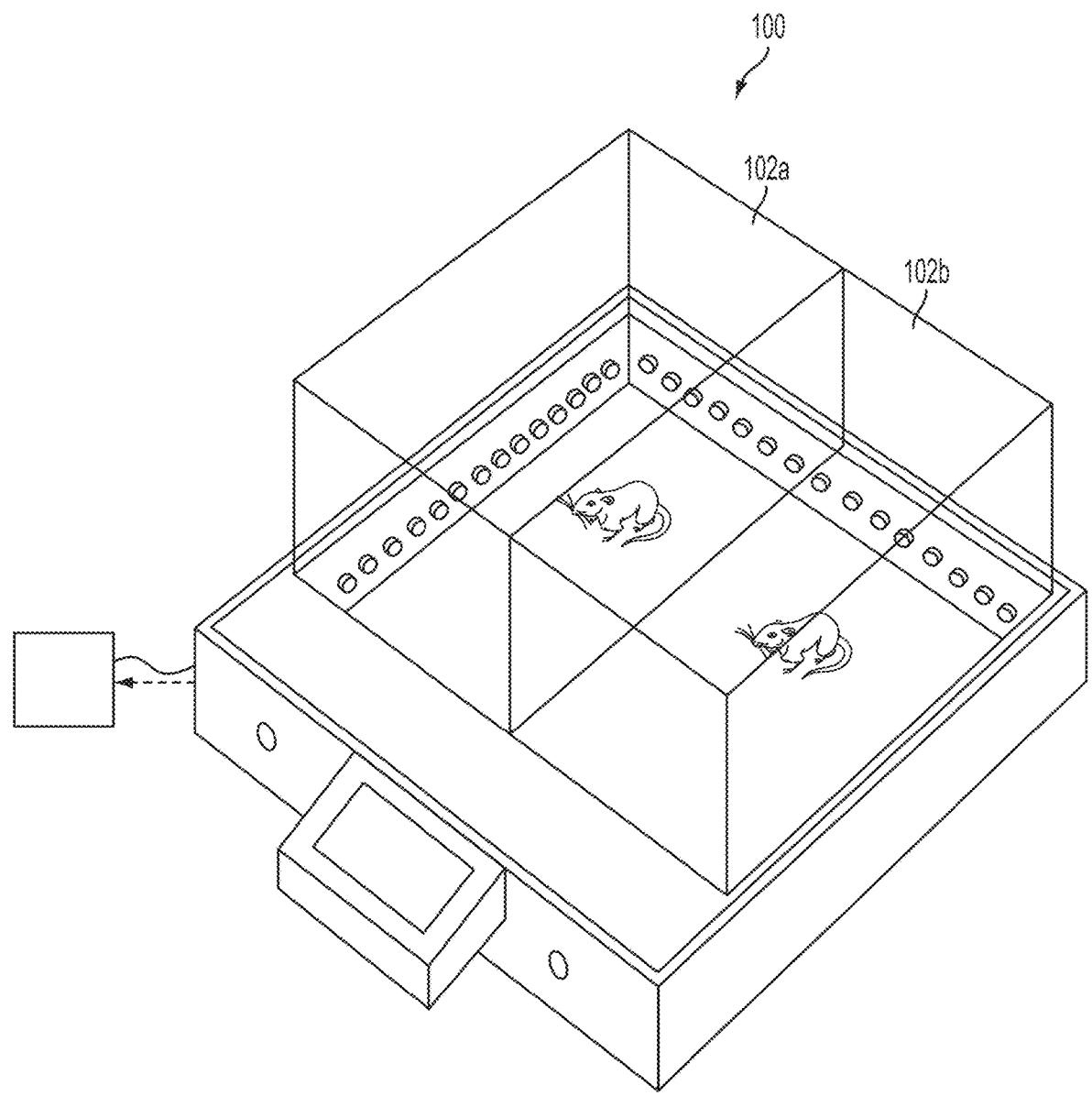
FIG. 2 is a perspective view of a device for monitoring animal behavior according to one embodiment.

Turning now to the figures, FIG. 1 shows a device 100 for monitoring animal behavior according to one embodiment. In some embodiments, monitoring animal behavior via the device 100 includes detecting and recording animal behavior. The device 100 includes a corral 102 defining a contained field within which a rodent 104 may be housed during a study. As shown in this figure, the corral 102 is an open field which allows the rodent 104 to freely move. Although only one corral 102 is shown in the device 100 of FIG. 1, the device 100 may have multiple corrals 102 in other embodiments. For example, as shown in FIG. 2, the device 100 may have two corrals 102a, 102b, each of which is shown to house a rodent 104 during a laboratory experiment. A person having skill in the art should appreciate that device 100 may have more than two corrals 102a, 102b in other embodiments, as this aspect of the disclosure is not limited in this regard. For example, the device 100 may have 6, 8, 10, 12, or even 20 corrals in other embodiments. A skilled artisan also should appreciate that although only one rodent 104 is shown in each of the corrals illustrated in FIGS. 1 and 2, the device 100 may conduct experiments with more than one rodent 104 per corral. For example, depending on the size of the corral 102 and on the experiment being conducted, each corral 102 may house 2, 4, 6, 8 or more rodents 104. A person having skill in the art should appreciate that each corral need not house the same number of rodents. For example, in one embodiment, a first corral 102a may house one rodent 104, while the second corral 102b may house more than one rodent 104. Without wishing to be bound by theory, by having a device configured to allow multiple rodents 104 to be housed in the same corral, and to monitor the behavior of each of the freely moving rodents 104, experiments relating to the social interactions, e.g., social anxiety, of the rodents 104 may be conducted.

Each corral 102 in the device 100 may be used to conduct separate experiments. Additionally, although the device 100 may conduct the same experiment in all of the corrals 102, in some embodiments, the device 100 may conduct different experiments in each corral 102. The device 100 also may be configured such that all the corrals 102 begin the experiment at the same time, although the device 100 may be configured such that the experiment being performed in each corral 102 begins at a different time. This may improve consistency in the testing, e.g., by allowing all the experiments to begin after the same amount of time has passed after each rodent has been genetically modified or stimulated instead of starting the experiments after different periods of time have passed.

In some embodiments, additional "dummy" corrals that are identical to the corrals 102 shown in FIGS. 1 and 2 are used to allow a first mouse (or group of mice) to be habituated to the test conditions while a second mouse (or group of mice) is being tested in the corrals 102.

Although the corrals 102 in FIGS. 1 and 2 are shown having a transparent upper enclosure 106, thus allowing observation of the rodents 104 from above the device, a person having skill in the art should appreciate that all or portions of the upper enclosure 106 also may be opaque. In some embodiments, the upper enclosure 106 includes black walls that prevent observation and light penetration via the top and sides of the upper enclosure 106.

As shown in FIG. 1, the device also includes a base surface 108 on which the rodents move and which is sensitive to the rodent's 104 paw print, toe print, or other inferior surface of the rodent. As shown in FIG. 1, the base surface 108 may be a transparent surface which allows observation of the rodent from below the device 100. For purposes herein, a transparent/clear surface may include a surface capable of allowing visible and/or non-visible light to pass therethrough. In some embodiments, the base surface 108 is the sensor of the device 100.

Figure 3:
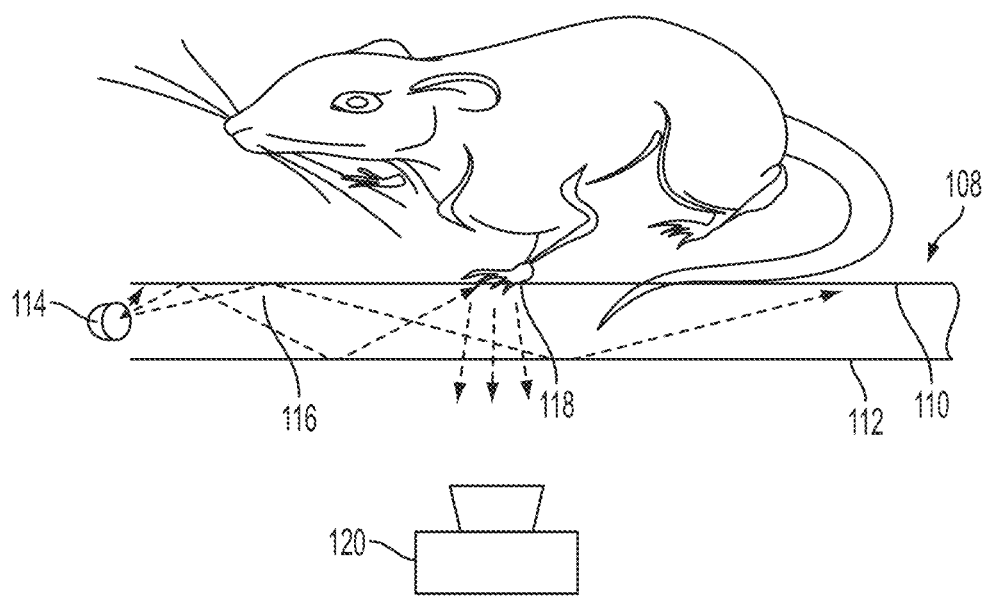
FIG. 3 is a cross-sectional side view of a base surface of a device for monitoring animal behavior according to one embodiment.

As shown in FIG. 3, the base surface 108 includes an upper base surface 110 and a lower base surface 112. In some embodiments, the base surface 108 is a glass, acrylic, or silicone material, although other suitable materials may be used as this aspect of the disclosure is not limited in this regard. In some embodiments, all or portions of the upper base surface 110 includes a textured surface which acts as a stimulus for the rodent(s) 104 in the corral 102.

As shown in FIGS. 1-3, lights 114, such as LEDs, are positioned around the perimeter of the base surface 108. In some embodiments, the lights 114 are mounted in a channel (not shown) within a movable rail. In such embodiments, the lights 114 and base structure 108 (e.g., a glass FTIR surface) may be easily separated for replacement of broken parts and to allow for optimal positioning of lights relative to an edge of the surface 108. In other embodiments, the lights 114 may be positioned as strip lights around the edge of the surface 108.

The lights 114 emit light which may include a non-visible band light, e.g. near-infrared, infrared, or ultraviolet light, or another suitable type of light. As shown in FIG. 3, the light emitted by the lights 114 is totally internally reflected (see e.g. at 116). When a rodent's 104 footprint, toe print, or other inferior surface comes into contact with the upper base surface 110, e.g. at 118, the internally reflected light becomes frustrated and is refracted out of the base surface 108 via the bottom base surface 112.

The device 100 also may include a light source beneath the sensor or panel to facilitate illumination of the inferior surfaces of the animal not in contact with the sensor. This lighting may be positioned beneath the sensor or panel in a location outside the perimeter of the chamber footprint to facilitate lighting of the subject animal within the chamber while keeping the light source or reflections thereof away from the view of a camera or imaging device, e.g., a capturing device 120.

In some embodiments, rodents (e.g., mice) are more active when the corral 102 is illuminated with a red or infrared lights, which are not visible to the rodents, than when the corral 102 is illuminated with a white light (e.g., a visible light). In such embodiments, the mice also may act more naturally when the corral is illuminated with red or infrared light. Without wishing to be bound by theory, mice are naturally active only when it is dark and remain dormant when it is light. Again, without wishing to be bound by theory, when mice are forced into a brightly illuminated space they show signs of stress. It was hypothesized that mice would become more active and behave more naturally when confined to a corral with little to no visible light, instead of a conventional brightly lit corral, and in one embodiment, it was observed that mice in a dark corral are active for a longer period of time than mice in a lit environment.

Figure 4:
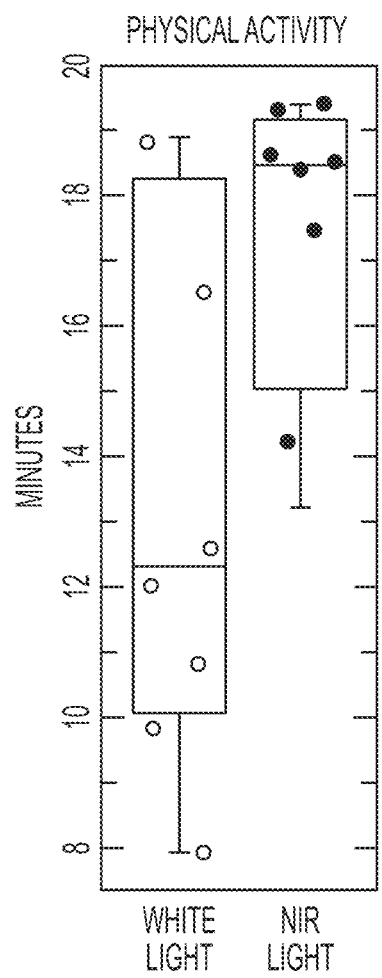
FIG. 4 is a graph showing a physical activity of mice in corrals lit by white light and by non-visible near infrared light.

For example, as illustrated in the graph in FIG. 4, when mice were observed for twenty (20) minutes in a translucent FTIR corral 102 illuminated from all sides with white light, the mice were physically active (e.g., walking, rearing, and grooming) for 13.41 minutes. In contrast, when the mice were placed in an opaque (e.g., "blackout") corral and were illuminated from below with only non-visible near infrared (NIR) light, the mice were physically active 19.39 of the 20 minutes.

While lighting the animal from beneath may inform a detection algorithm of the relative positions of the head and tail of the animal, this added light also may reduce the dynamic range of the FTIR signal. In some embodiments, to maintain the full dynamic range of the FTIR signal, the under lighting may be turned on only on alternating or for intermittent video frames. In such embodiments, this illumination strategy may permit recording of separable data streams of the same animal behavior from one capturing device 120 (e.g., a video camera), with one data stream being used for dynamic range of FTIR-generated foot position data and the other being used for orientation and analysis of body position.

Figure 5:
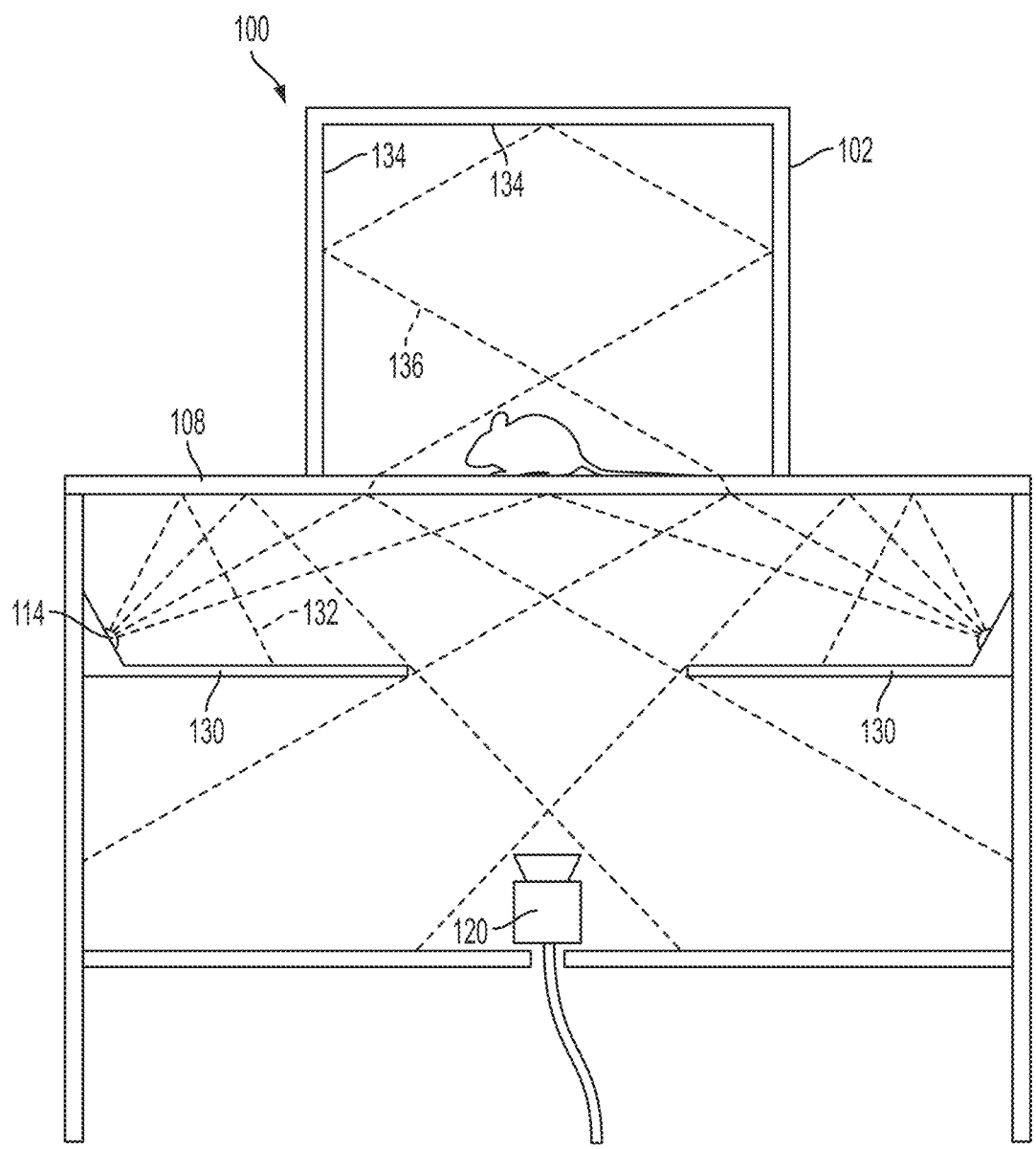
FIG. 5 is a cross-sectional side view of a device for monitoring animal behavior according to another embodiment.

In some embodiments, for automated scoring of video data, the field of view beyond the subject (e.g., rodent) is configured to be uniform in color and light intensity. To optimize the data, a lighting configuration may be used that permits a freely behaving animal to be uniformly illuminated without generating any visible light or reflections of light in the field of view beyond the animal from the viewpoint of the capturing device. As shown in FIG. 5, the capturing device 120 (e.g., a camera) is positioned below a transparent base surface 108 of the corral 102 and an opaque divider 130 is positioned between the corral 102 and the capturing device 120. The divider 130 may have a cutout that permits full view of the corral base surface 108 from the capturing device 120, while the field of view beyond the corral 102 is occluded. In some embodiments, the surface finish of the opaque divider 130 is matte to minimize secondary reflections. Lights 114 may be positioned so that the capturing device 120 is shadowed from rays of light 132 reflected off of lower base surface 112 of the corral base surface 108. To prevent illumination of the interior surfaces of the corral 102 from the viewpoint of the capturing device 120, the corral walls and ceiling (collectively, 134) may be constructed from an opaque material with a reflective surface and may be positioned so that reflected light rays 136 exiting the corral 102 are reflected away from the aperture of the capturing device 120.

As shown in FIG. 3, the capturing device 120 of the device 100 may be located below the lower base surface 112 for capturing the refracted light. In some embodiments, the capturing device 120 may be located in the housing 122 (see FIG. 1) of the device, although, in other embodiment the capturing device 120 may be separate from the device 100. The capturing device 120 may cooperate with the base surface 108 to capture a profile of the rodent's 104 full footprint, toe print when the rodent 104 is standing on its toes, or other inferior surface (e.g., the rodent's 104 abdomen).

Figure 6A:
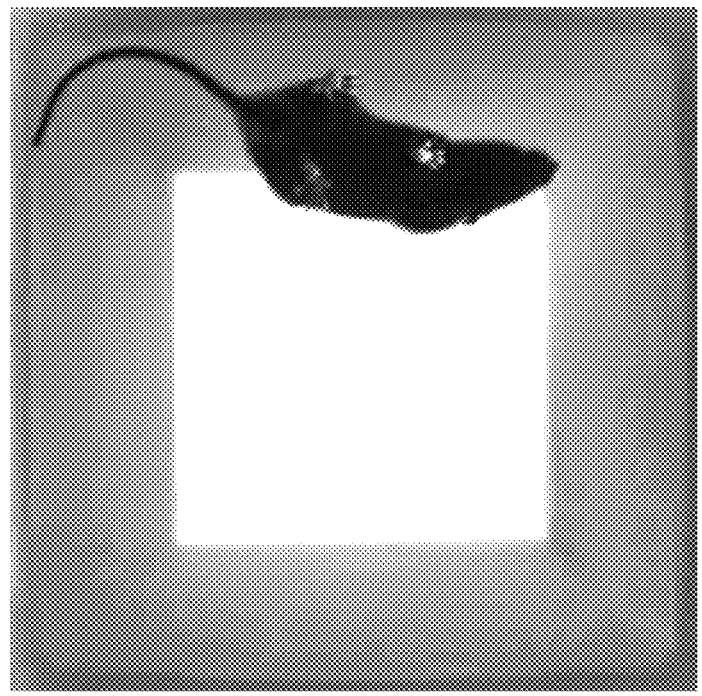
FIGS. 6A-6J are images representing screen shots of recordings captured by a capturing device according to various embodiments, each showing a rodent making contact with a base surface.
Figure 6B:
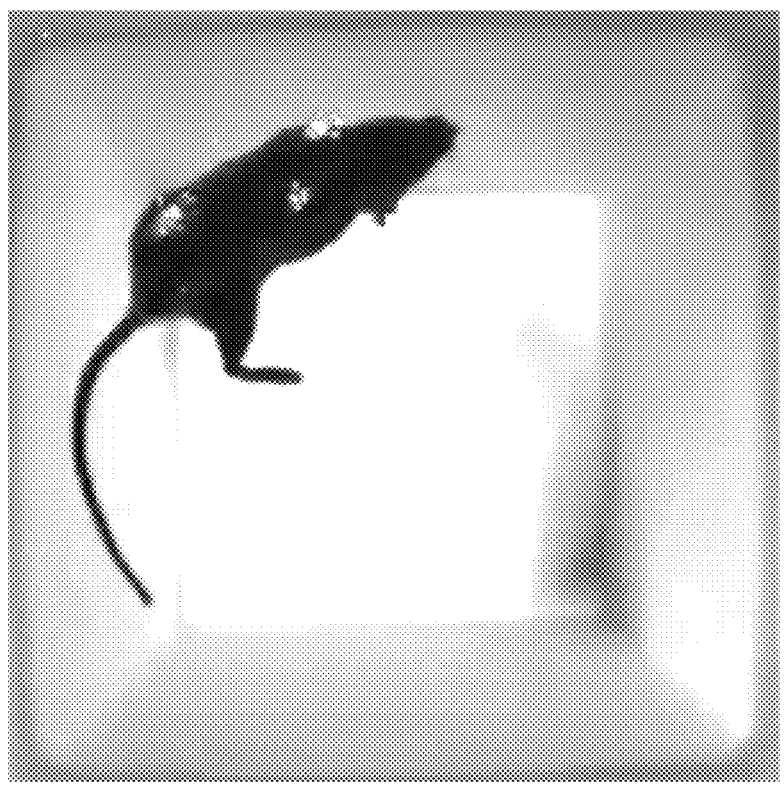
Figure 6C:
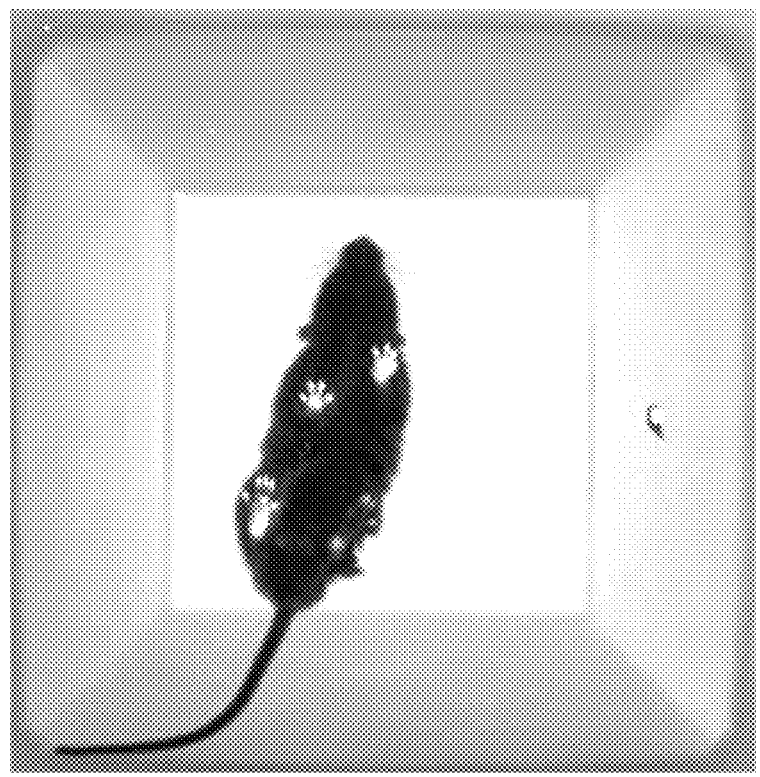
Figure 6D:
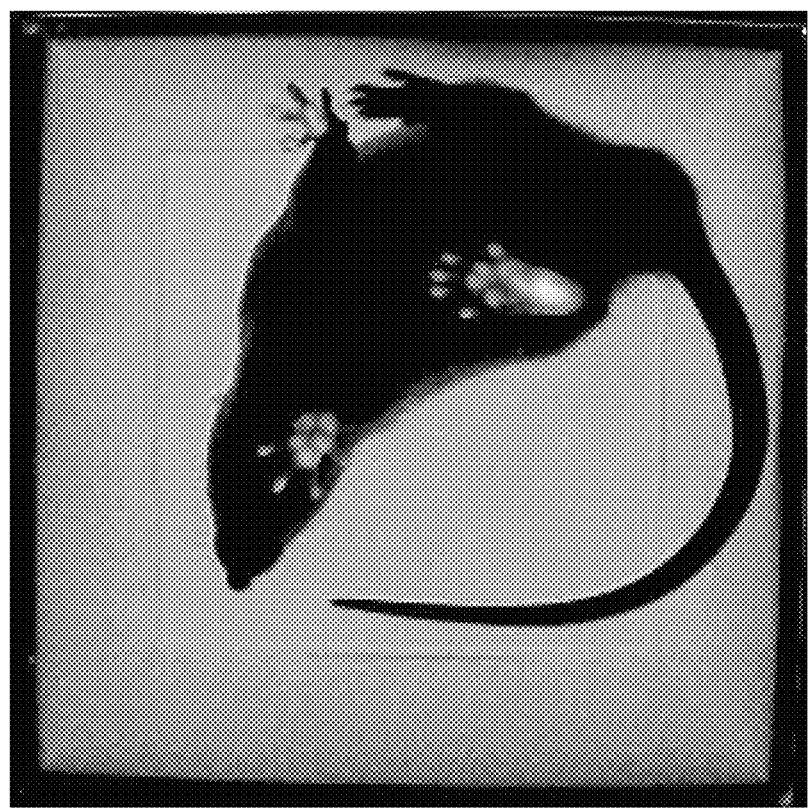
Figure 6E:
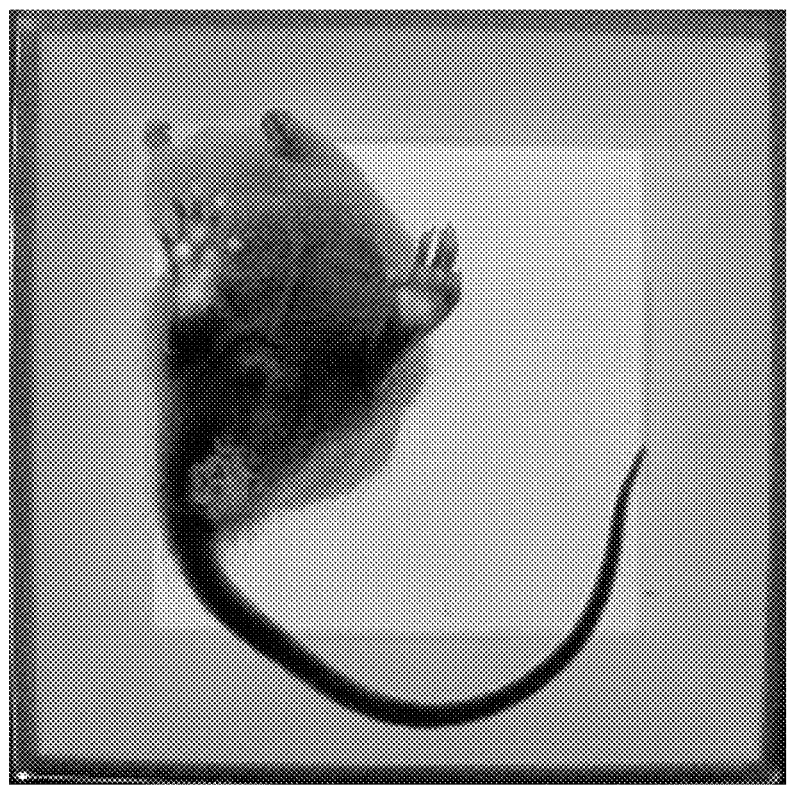
Figure 6F:
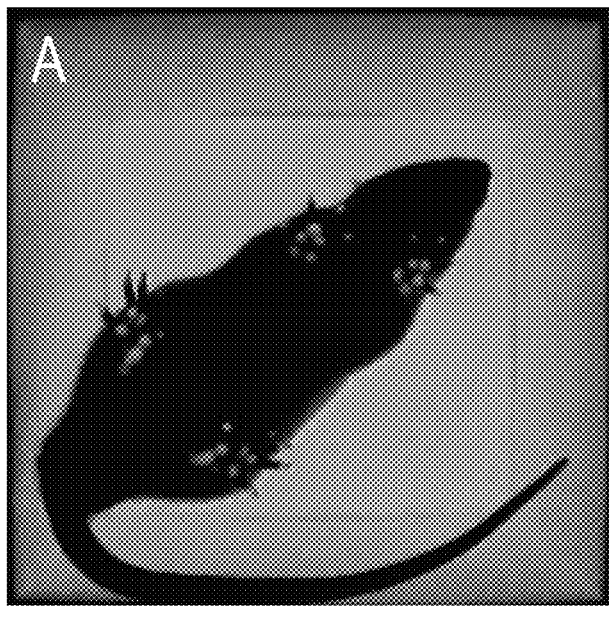
Figure 6F:
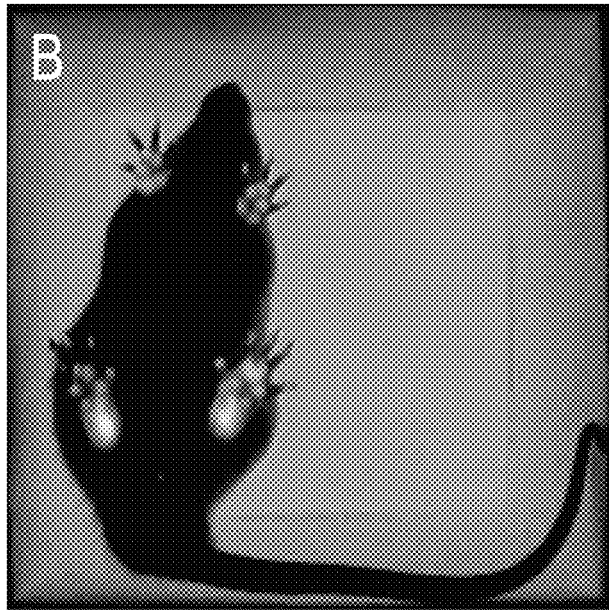
Figure 6G:
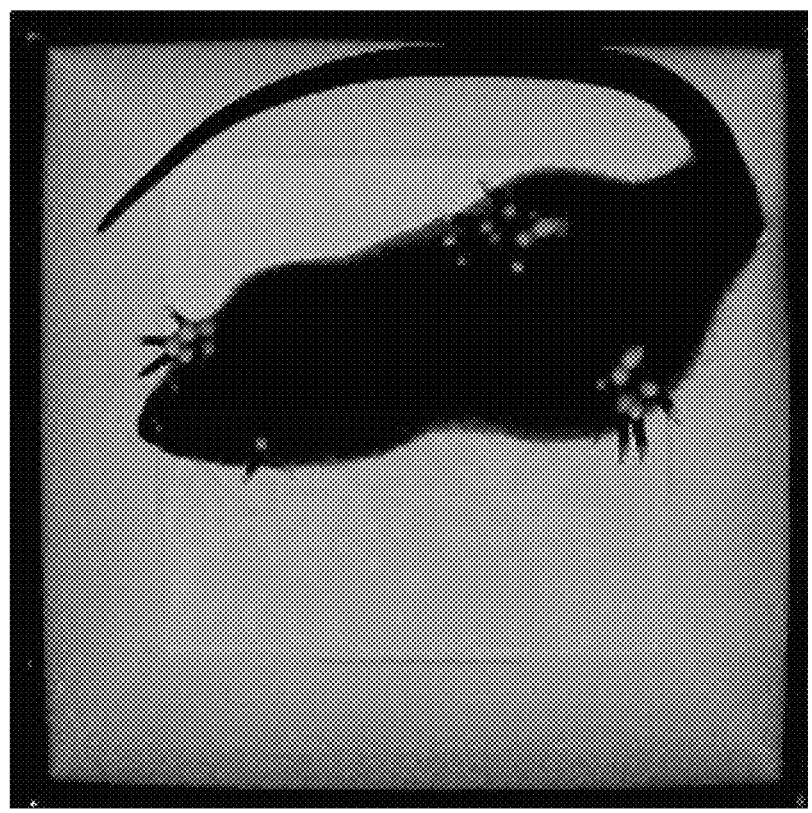
Figure 6H:
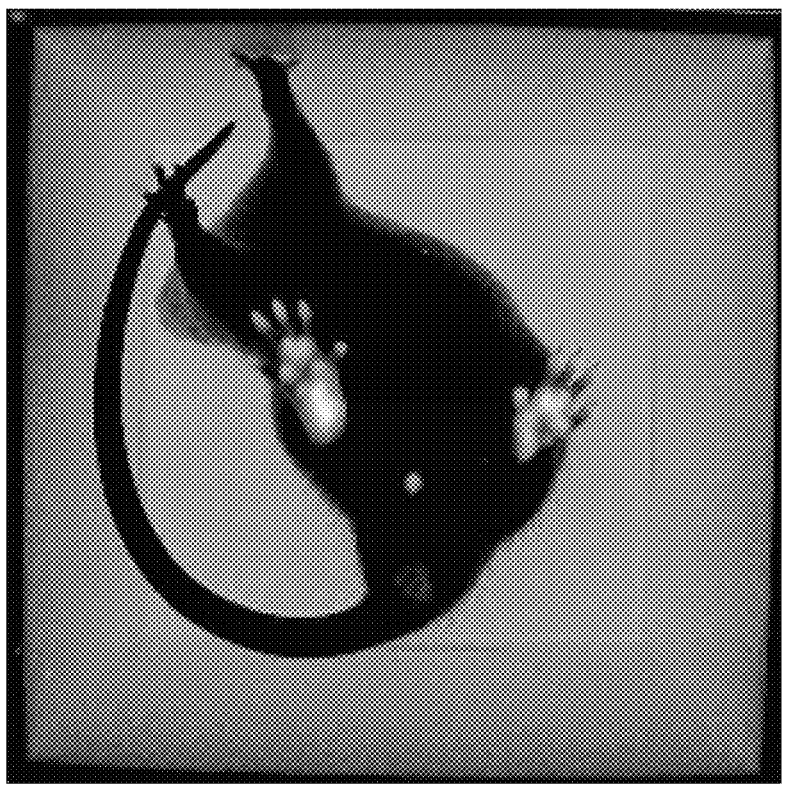
Figure 6I:
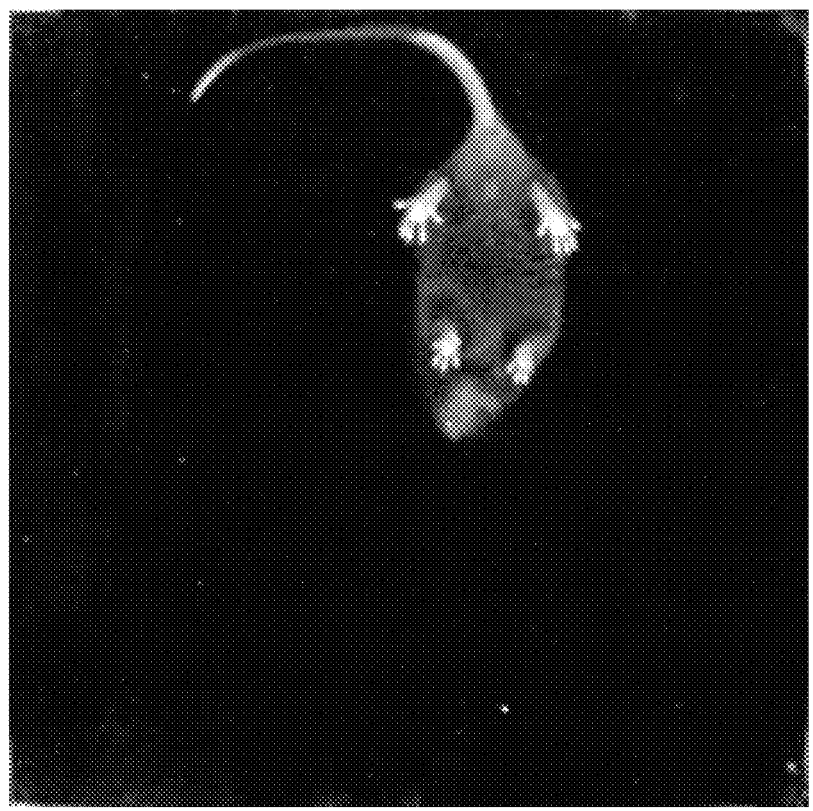
Figure 6J:

Examples of recordings captured by an exemplary capturing device can be seen in FIG. 6A-6J, which represent screen shots of the recordings taken by a video camera. FIG. 6A shows a Naïve mouse according to one embodiment. FIG. 6B shows the mouse of FIG. 6A twenty-four hours after a nerve injury. FIG. 6C shows the mouse of FIG. 6A twenty-one days after the nerve injury. FIG. 6D shows a Naïve rat according to another embodiment. FIG. 6E shows the rat of FIG. 6D twenty-four hours after an adjuvant-evoked injury to the rat's left hind paw. FIG. 6F illustrates how rats show increasing footprint irradiance upon habituation in an infrared-FTIR device enclosure. As shown in FIG. 6F, "tiptoeing" behavior often returns when an individual enters the room or upon loud noise such as clapping (e.g., handclapping). FIG. 6G illustrates a rat with no habituation. FIG. 6H shows the rat of FIG. 6G after twenty-minutes have passed. FIG. 6I illustrates FTIR in dark and underlit conditions. FIG. 6J shows spontaneous injuries that are detected in a Naïve mouse. These images reveal that rodents in a more relaxed state exhibit more full-foot contact as opposed to rodents in a more anxious state that exhibit substantially toe-only contact.

Figure 7A:
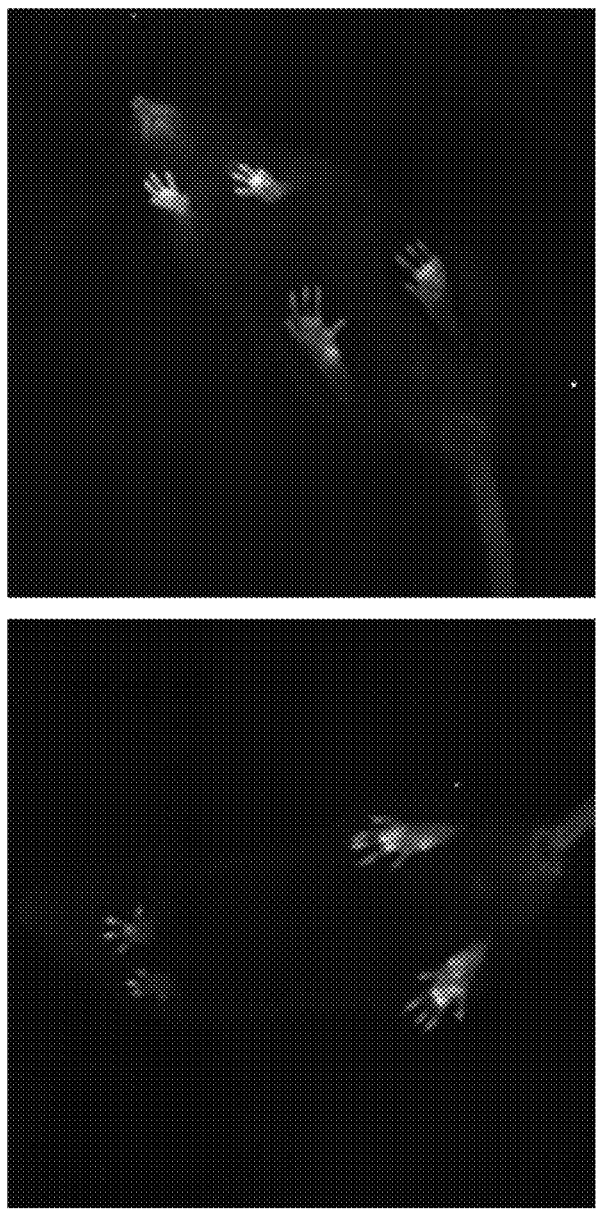
FIG. 7A-7B are images representing screen shots of recordings captured by a capturing device according to other embodiments, each showing a rodent making contact with a base surface.
Figure 7B:
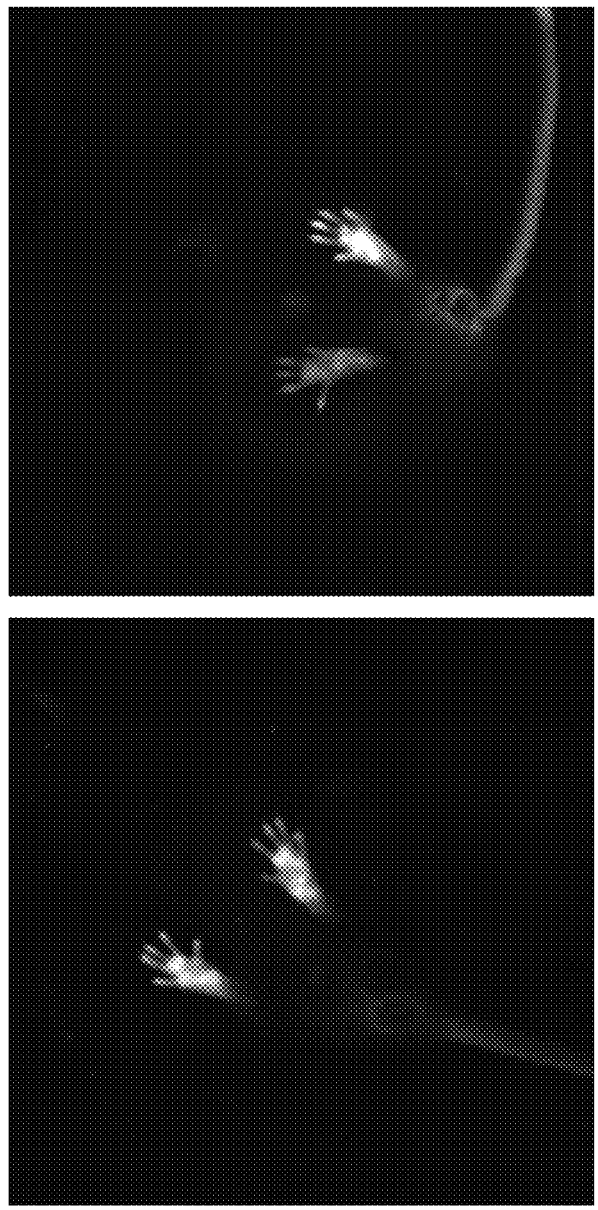

FIGS. 7A and 7B illustrate examples of FTIR recordings showing distinct pain-related behaviors in mouse models of abdominal pain and distinct pain-related behaviors when a mouse paw is injured, respectively. As shown in FIG. 7A at left, naïve mice walk with their weight shifted towards their hindpaws, which results in increased FTIR luminance of the hindpaws in this figure. In FIG. 7A at right, an embodiment showing abdominal pain, the mice shift their weight to their forepaws while walking. In such an embodiment, there is increased FTIR luminance of the forepaws as compared to that of the naïve mice shown in FIG. 7A at left.

FIG. 7B at left shows a naïve mouse standing on its hindpaws while grooming. In this embodiment, the luminance of each hind paw is substantially similar. When a mouse has been injured in a spontaneous fight with another mouse, for example, the location of injury is indicated by different FTIR luminance for each hind paw. As shown in FIG. 7B, at right, the mouse has an fight-related injury to its right hind leg above the knee joint, which causes a reduced FTIR luminance in the paw nearest the injured limb. Stated differently, in such embodiments, mice with a spontaneous leg injury shift their weight to the uninjured leg (which has a greater FTIR luminance).

Figure 8:
FIG. 8 are images representing screen shots of recordings captured by a capturing device according to another embodiment, each showing a rodent making contact with a base surface.

FIG. 8 illustrates examples of FTIR recordings that detect analgesic efficacy, with great sensitivity. FIG. 8 at left shows a mouse after an experimental induction of inflammation, and presumably pain, in its left hind paw. FIG. 8 at right shows a mouse that has underwent the same experimental induction of inflammatory pain in the left hind paw as the mouse in FIG. 8 at left, but has also been given an analgesic (e.g., diclofenac) before FTIR imaging. As shown in these embodiments, the mouse treated with the analgesic does not shift its weight to the uninjured leg like the mouse that was not treated with the analgesic.

FIG. 8 also demonstrates the capability of the device to detect not only the form of the contact areas of the paw, but also the relative pressures exerted within the contact areas of the paws (e.g., by showing the differences in light intensity). For example, the FTIR images are brighter in areas where there is greater relative pressure exerted by the hind paw than in areas where there is less relative pressure exerted.

In some embodiment, the capturing device 120 is a camera for recording the movement of the rodent or rodents. The camera may be a near-infrared camera in some embodiments, although other types of cameras may be employed as this aspect of the disclosure is not limiting. Without wishing to be bound by theory, the type of capturing device 120 corresponds to the type of band light emitted by the lights 114. For example, in embodiments in which a near-infrared band light is emitted by the lights 114, a near-infrared camera is used.

In some embodiments, the device 100 is configured such that images of the topographical features representing the inferior surface of each freely roaming rodent or rodents 104 in a single corral 102 may be separately analyzed. Without wishing to be bound by theory, the behavior of the rodent(s) 104 may be compared with either or both the behavior of other rodent(s) 104 in the same corral 102 and the behavior of any rodent(s) in other corrals 102.

As shown in FIG. 1, the device 100 also may have a control panel 124, such as a touch screen control panel, for controlling various parameters of the device 100, e.g. the stimulus applied in the corral 102. In some embodiments, the device 100 is connected to one or more control devices 126, which may be used to control the device 100. The control device 126 may be a computer (desktop or laptop), a tablet, a mobile device, or any other suitable apparatus for controlling the device 100. As shown in FIG. 1, the device 100 may be directly connected 128*a* to the control device 126 (e.g., via a USB connection) or the device 100 may be indirectly connected 128*b* to the control device 126. The indirect connection 128*b* may include an internet, intranet, wireless, or other network connection suitable for indirectly connecting the control device 126 to the device 100. The control device 126 may run an application configured to store the images collected by the capturing device 120 and to process the images and/or convert the images into another data format for analysis. Other processing and/or analysis also may be performed by the device 100 itself and/or by the control device 126.

Figure 9:
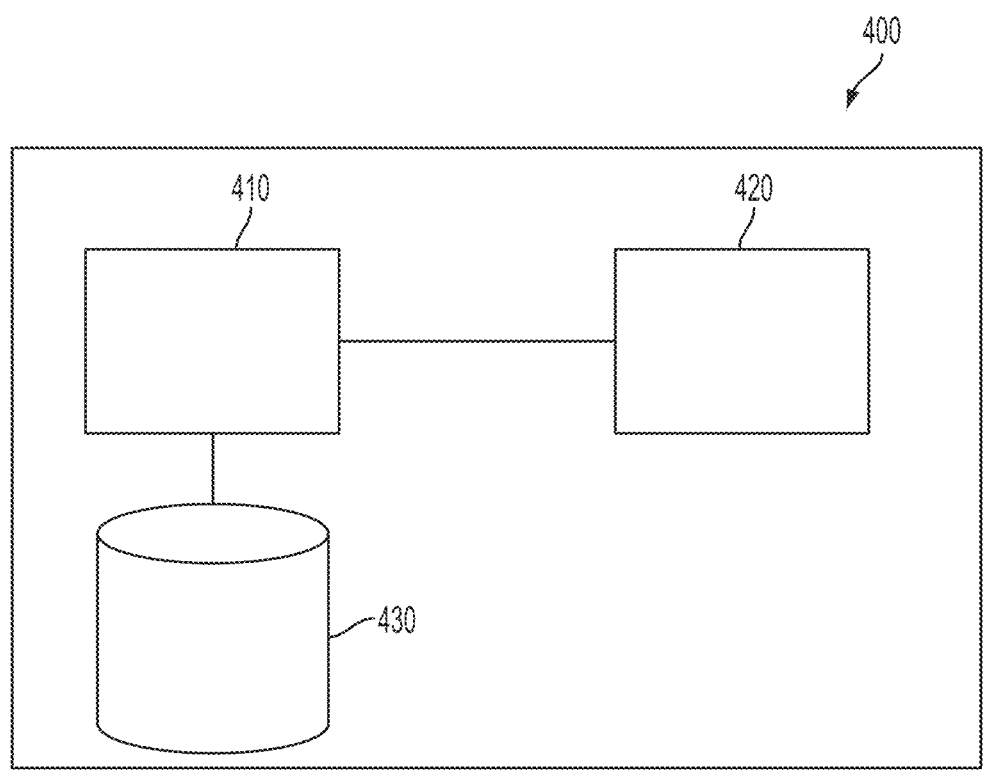
FIG. 9 is a schematic view of a computer system according to one embodiment.

The control device 126 in accordance with the techniques described herein may take any suitable form, as aspects of the present invention are not limited in this respect. An illustrative implementation of a computer system 400 that may be used in connection with some embodiments of the present invention is shown in FIG. 9. One or more computer systems such as computer system 400 may be used to implement any of the functionality described above. The computer system 400 may include one or more processors 410 (e.g., processing circuits) and one or more computer-readable storage media (i.e., tangible, non-transitory computer-readable media), e.g., volatile storage 420 (e.g., memory) and one or more non-volatile storage media 430, which may be formed of any suitable non-volatile data storage media. The processor(s) 410 may control writing data to and reading data from the volatile storage 420 and/or the non-volatile storage device 430 in any suitable manner, as aspects of the present invention are not limited in this respect. To perform any of the functionality described herein, processor(s) 410 may execute one or more instructions stored in one or more computer-readable storage media (e.g., volatile storage 420), which may serve as tangible, non-transitory computer-readable media storing instructions for execution by the processor 410.

The above-described embodiments of the present invention can be implemented in any of numerous ways. For example, the embodiments may be implemented using hardware, software or a combination thereof. When implemented in software, the software code (e.g., instructions) can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of embodiments of the present invention comprises at least one computer-readable storage medium (i.e., at least one tangible, non-transitory computer-readable medium, e.g., a computer memory, a floppy disk, a compact disk, a magnetic tape, or other tangible, non-transitory computer-readable medium) encoded with a computer program (i.e., a plurality of instructions), which, when executed on one or more processors, performs above-discussed functions of embodiments of the present invention. The computer-readable storage medium can be transportable such that the program stored thereon can be loaded onto any computer resource to implement aspects of the present invention discussed herein. In addition, it should be appreciated that the reference to a computer program which, when executed, performs above-discussed functions, is not limited to an application program running on a host computer. Rather, the term "computer program" is used herein in a generic sense to reference any type of computer code (e.g., software or microcode) that can be employed to program one or more processors to implement above-discussed aspects of the present invention.

In using the device 100, in one exemplary embodiment, at least a subset of a group of rodents is obtained and placed in one or more corrals 102 of the device 100. For purposes herein, a subset of rodents may include one or more rodents. In some embodiments, a first subset of rodents is placed in the corral 102 and isolated from another subset of rodents. In some embodiments, the rodents are genetically modified prior to placement in the corral 102. For example, the rodent may be optogenetically modified for manipulation of genetically encoded light-sensitive proteins to study the function of molecules, synapses, cells, and systems. There also may be proteins or other molecules given to the rodent. The device 100 may be enabled, either before or when the rodents are placed in the corral 102 such that the lights 114 emit band light which is totally internally reflected within the base surface 108.

Next, a stimulus may be applied to the rodents. In some embodiments, a light stimulus is applied by delivering a light through the base. The light stimulus may include different wavelengths of light and/or different patterns of light. In another embodiment, a thermal stimulus may be applied. For example, the base surface 108 maybe heated or cooled and/or the entire corral may be heated or cooled. In other embodiments, the rodents are subjected to pain stimulus. In some embodiments, the rodents 104 are subjected to different levels and types noises. The rodents also may be exposed to different smells. In some embodiments, multiple rodents are placed in the same corral to observe social interactions between the rodents. The applied stimulus may be delivered through the base surface 108 in some embodiments, although, in other embodiments, the stimulus may be delivered through alternate methods.

For devices performing a study using multiple rodents (whether in the same corral or in different corrals), the rodents may be stimulated with the same stimulus or with different stimuli. Additionally, the animals may receive only one stimulus or several different stimuli. The device 100 also may be configured such that the rodents are tested for short periods of time and/or for extended periods of time.

The behavior of the rodents, both before and after the stimulus, may be observed by imaging the spatial extent and intensity of signal of the footprint, toe print, and/or other inferior surface of the animal in response to the stimulus and its change over time. For example, in some embodiments, the rodents may get anxious and stand up on their toes creating a distinctive footprint, which differs from the more flattened footprint created when the rodents have settled down. The image is generated as a result of contact between the footprint or toe print, or other inferior surface of the rodent, and the base surface 108, which frustrates the band light and causes the light to be reflected and to exit the base surface 108 for detecting by the capturing device 120. The capturing device 120 captures the illuminated areas on the base surface 108 and these images are collected and analyzed.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A method of detecting and recording behavioral information of a group of animals in a corral, the method comprising:
   emitting band lights into a base surface of the corral via a plurality of lights positioned around the base surface, the band lights being totally internally reflected within the base surface, the base surface being sensitive to a footprint of one or more animals in the corral such that contact between the footprint of the one or more animals frustrates the totally internally reflected light and refracts the light out of the base surface; and
   capturing an image of both a full footprint of a first animal and an image of a toe print of the first animal when the first animal is standing on its toes.

2. The method of claim 1, wherein capturing the image includes detecting refracted light when the first animal contacts the base surface.

3. The method of claim 2, wherein capturing includes detecting refracted light resulting from contact between a foot and a toe of the first animal and the base surface.

4. The method of claim 1, wherein capturing the image includes capturing the image of both the full footprint of the first animal and the image of the toe print of the first animal via an image capture device.

5. The method of claim 4, wherein capturing the image includes capturing the image via the image capture device positioned beneath the base surface.

6. The method of claim 1, wherein capturing includes capturing a spatial extent and intensity of a profile of the full footprint of the first animal and a profile of the toe print of the first animal and capturing a change of the profiles over time.

7. The method of claim 1, further comprising capturing an image of the whole first animal independent of surface contact between the first animal and the base surface in conditions that mimic day or night.

8. The method of claim 1, wherein emitting band lights includes emitting non-visible band lights into the base surface.

9. The method of claim 1, further comprising:
   stimulating the first animal with a first stimulus; and
   observing a resulting behavior of the first animal via imaging both the footprint and the toe print of the first animal in response to the first stimulus.

10. The method of claim 9, wherein stimulating includes stimulating the first animal via at least one of a light stimulus, a temperature stimulus, or a texture stimulus.

11. The method of claim 10, wherein stimulating the first animal includes stimulating the first animal via the base surface.

12. The method of claim 11, wherein stimulating the first animal via the base surface includes delivering light through the base surface.

13. The method of claim 12, wherein delivering light includes delivering light having different wavelengths or different patterns.

14. The method of claim 9, further comprising:
   stimulating a second animal with a second stimulus; and
   observing a resulting behavior of the second animal via imaging both a footprint and a toe print of the second animal in response to the second stimulus.

15. The method of claim 14, wherein imaging both the footprint and the toe print of the second animal includes capturing an image of both the full footprint of the second animal and an image of the toe print of the second animal when the second animal is standing on its toes.

16. The method of claim 15, wherein capturing the image includes detecting refracted light when the second animal contacts the base surface.

17. The method of claim 14, wherein stimulating the second animal comprises stimulating the second animal with a second stimulus that is different from the first stimulus.

18. The method of claim 1, further comprising supplying the group of animals for behavioral monitoring.

19. The method of claim 18, wherein supplying the group of animals includes supplying a group of genetically modified animals.

20. The method of claim 1, wherein the base surface is transparent.

21. The method of claim 20, wherein the base surface includes a glass or plastic material.

* * * * *